United States Patent [19]

Giurtino et al.

[11] Patent Number: 5,697,949

[45] Date of Patent: Dec. 16, 1997

[54] SMALL DIAMETER ENDOSCOPIC INSTRUMENTS

[75] Inventors: Joel F. Giurtino; George Nunez, both of Miami, Fla.

[73] Assignee: Symbiosis Corporation, Miami, Fla.

[21] Appl. No.: 443,466

[22] Filed: May 18, 1995

[51] Int. Cl.⁶ ............................................. A61B 17/36
[52] U.S. Cl. .......................... 606/205; 606/46; 606/51; 606/206
[58] Field of Search .................... 606/41, 42, 45–52, 606/205–208; 128/751

[56] References Cited

U.S. PATENT DOCUMENTS

| | | | |
|---|---|---|---|
| 5,085,658 | 2/1992 | Meyer | 606/46 |
| 5,133,727 | 7/1992 | Bales et al. | 606/170 |
| 5,171,256 | 12/1992 | Smith et al. | 606/205 |
| 5,241,968 | 9/1993 | Slater | 128/751 |
| 5,254,130 | 10/1993 | Poncet et al. | 606/206 |
| 5,300,087 | 4/1994 | Knoepfler | 606/207 |
| 5,312,434 | 5/1994 | Crainich | 606/207 |
| 5,330,502 | 7/1994 | Hassler et al. | 606/205 |
| 5,342,381 | 8/1994 | Tidemand | 606/174 |
| 5,352,223 | 10/1994 | McBrayer et al. | 606/51 |
| 5,354,311 | 10/1994 | Kambin et al. | 606/205 |
| 5,395,369 | 3/1995 | McBrayer et al. | 606/51 |
| 5,396,900 | 3/1995 | Slater et al. | 128/751 |
| 5,403,342 | 4/1995 | Tovey et al. | 606/205 |
| 5,507,772 | 4/1996 | Shutt et al. | 606/205 |

Primary Examiner—Jennifer Bahr
Assistant Examiner—Michael Peffley
Attorney, Agent, or Firm—David P. Gordon

[57] ABSTRACT

An endoscopic instrument includes a small diameter hollow tube, an axially displaceable wire extending through the tube, a manual actuator coupled to the proximal ends of the tube and wire for axially displacing the wire relative to the tube, a first end effector mechanically coupled to the distal end of the tube and having a proximal portion which is provided with a curved guiding channel which receives and guides a distal portion of the wire, and a second end effector mechanically coupled to the distal end of the displaceable wire and rotatably coupled to the first end effector. When arranged as a bipolar instrument, the tube and pull wire are conductive, the pull wire is covered with an electrically insulating sheath except at its very distal end, the first end effector is conductive and partially insulated and is electrically coupled to distal end of tube, and the second end effector is conductive and partially insulated and electrically coupled to the distal end of the pull wire. Both end effectors are preferably cast alloy partially coated with PTFE, and are rotatably coupled to each other with the aid of an insulating ceramic bushing-washer. According to one embodiment, the first end effector is provided with an integral axle pin. The provided endoscopic instrument, when the tube is 1.7 mm in diameter, is particularly useful in endoscopic neurological procedures.

20 Claims, 4 Drawing Sheets

5,697,949

1

SMALL DIAMETER ENDOSCOPIC INSTRUMENTS

BACKGROUND OF THE INVENTION

1. Field of the Invention

The present invention relates to endoscopic surgical instruments. More particularly, the present invention relates to a very small diameter bipolar single acting endoscopic surgical forceps/clamp. While not limited, the invention has particular use with respect to neurologic procedures.

2. State of the Art

Endoscopic surgery is widely practiced throughout the world today and its acceptance is growing rapidly. Broadly speaking, endoscopic surgery includes colo-rectal surgery through an endoscope, arthroscopic surgery, laparoscopic surgery, and neuro-surgery. In all cases other than the colo-rectal surgery, the endoscopic surgery requires insertion of an endoscopic instrument through a first port (often formed by a trocar), and use of a camera which is inserted through a second port. With multiple ports, organs or tissue may be grasped with one surgical instrument, and simultaneously may be cut with another surgical instrument; all under view of the surgeon via the camera in place in one of the ports.

By 1996, it is expected that more than two million additional endosurgeries will be performed per year that, in 1990, were done via open surgery (MedPRO Month, I:12, p. 178). The advantages of endoscopic surgery are clear in that it is less invasive, less traumatic and recovery is typically quicker. This is particularly so in neuro-surgery involving the central nervous system where one or more instruments are inserted through small holes in the neck and/or skull of the patient. Endoscopic techniques are highly preferred in neurosurgery since open surgery entails removing at least part of the skull, resulting in severe trauma and surgical morbidity.

Endoscopic surgical instruments generally include a coil or tube (hereinafter broadly referred to as a tube), a pull wire or push rod which extends through the tube, an actuating means engaging the tube and the pull wire or push rod for imparting reciprocal axial motion to the pull wire or push rod, end effector means coupled to the pull wire or push rod, and a clevis coupled to the tube at its proximal end and to the end effector means at its distal end, wherein axial movement of the pull wire or push rod effects movement of the end effector means in a plane parallel to the longitudinal axis of the push rod. For purposes herein, the "distal end" of a surgical instrument or any part thereof, is the end most distant from the surgeon and closest to the surgical site, while the "proximal end" of the instrument or any part thereof, is, the end most proximate the surgeon and farthest from the surgical site.

Bipolar cauterization endoscopic surgical instruments are well known in the art. For example, co-assigned U.S. Pat. No. 5,352,223 discloses a bipolar endoscopic forceps having a hollow conductive tube, an insulated conductive push rod which extends through the tube, and a pair of conductive end effectors (grippers) coupled respectively to the distal end of the tube and the push rod. The end effectors are insulated from each other and bipolar cautery current is applied to the respective end effectors via the tube and the push rod.

As mentioned above, most endoscopic instruments are designed to enter the body through an instrument port. Typically, these ports are either 5 mm or 10 mm in diameter and permit similarly sized instruments to pass therethrough.

2

It should be appreciated, however, that the relatively small size of endoscopic instruments poses a significant challenge in their design and manufacture. This is particularly so in bipolar instruments which must, by their nature, include moving parts which are electrically insulated from each other. The instrument described in the coassigned U.S. Pat. No. 5,352,223 patent, like most endoscopic instruments, is designed to be used with a 5 mm or 10 mm instrument port (trocar tube). However, in neuro-surgery, even 5 mm instruments are larger and more invasive than desired. Thus, even smaller instruments are preferred.

SUMMARY OF THE INVENTION

It is therefore an object of the invention to provide an endoscopic instrument which is substantially smaller in diameter than conventional endosurgical instruments.

It is another object of the invention to provide an endoscopic neurosurgical instrument having bipolar capability.

It is also an object of the invention to provide a bipolar endoscopic instrument which is small enough to enter the body through a 2 mm instrument port.

If is a further object of the invention to provide a very small diameter bipolar endoscopic forceps/clamp having a relatively large torque.

In accord with these objects which will be discussed in detail below, the endoscopic instrument of the present invention broadly includes a hollow tube having a diameter of approximately 1.7 mm, an axially displaceable wire extending therethrough, a manual actuation means coupled to the proximal ends of the tube and wire for axially displacing one of the tube and wire relative to the other, a first end effector mechanically coupled to the distal end of the tube and having a proximal portion which is provided with a curved guiding channel which receives and guides a distal portion of the wire, and a second end effector mechanically coupled to the distal end of the displaceable wire and rotatably coupled to the first end effector. Where the instrument is arranged to be a bipolar instrument, the tube and pull wire are conductive, the pull wire is covered with an electrically insulating sheath except at its very distal end, the first end effector is conductive and partially insulated and is electrically coupled to distal end of tube, and the second end effector is conductive and partially insulated and electrically coupled to the distal end of the pull wire. In addition, in the bipolar embodiment, the manual actuation means is preferably provided with a pair of electrical couplings for coupling respective poles of a source of bipolar cautery to the tube and wire.

In accord with preferred aspects of the invention, the first end effector is preferably a cast alloy which is coated with a polymeric insulation such as polytetrafluoroethylene (PTFE or TEFLON®) on at least a portion of its surface. The second end effector is also preferably a cast alloy which is coated with insulation such as PTFE on at least a portion of its surface. A proximal portion of the second end effector is provided with a tang for electrically and mechanically coupling it to the distal end of the displaceable wire. The end effectors are rotatably coupled to each other with the aid of an insulating ceramic bushing-washer.

According to one embodiment, the first end effector is provided with an integral axle pin having a deformable end and the second end effector is provided with a mounting hole. According to another embodiment, both end effectors are provided with mounting holes and they are coupled to each other with a stainless steel rivet and the insulating ceramic bushing-washer.

DETAILED DESCRIPTION OF THE PREFERRED EMBODIMENTS

Figure 1:
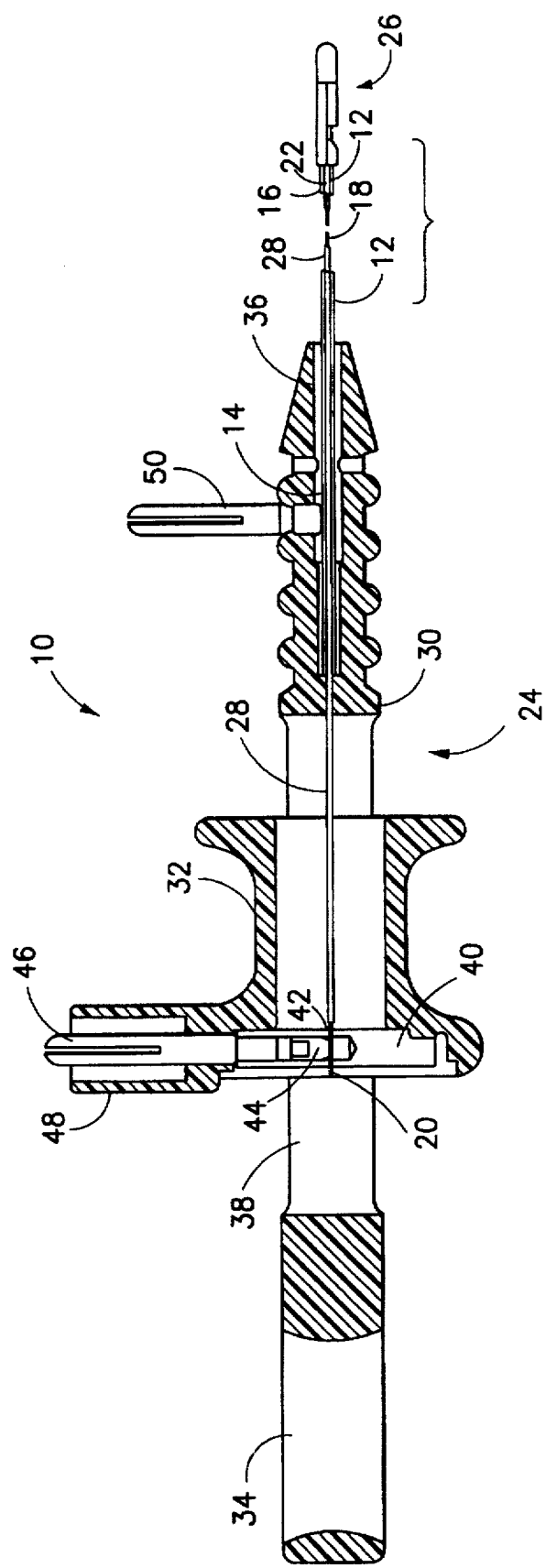
FIG. 1 is a partially transparent side elevation view in partial station of a bipolar forceps according to the invention.
Figure 2:
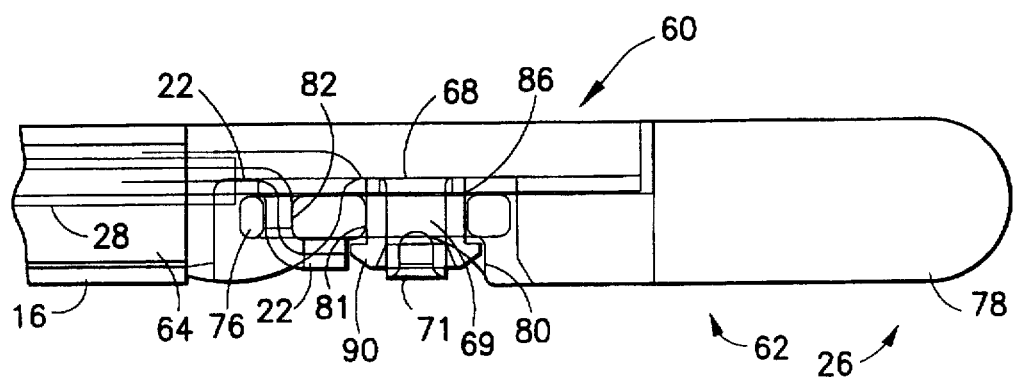
FIG. 2 is an art enlarged broken transparent view of the end effectors of FIG. 1 looking perpendicular to the axis of rotation.

Referring now to FIG. 1, a small diameter bipolar forceps 10 according to the invention generally includes a hollow conductive tube 12 having a proximal end 14 and a distal end 16, a conductive pull wire 18 extending through the tube 12 and having a proximal end 20 and a distal end 22, a proximal actuating handle 24, and a distal end effector assembly 26. According to the presently preferred embodiment, the conductive tube has an outer diameter of approximately 1.7 mm. The conductive pull wire 18 is provided with an insulating sheath 28 which extends along substantially its entire length except for a portion of its proximal end 20 and a portion of its distal end 22. The proximal actuating handle 24 has a central shaft 30 and a displaceable spool 32. The proximal end of the shaft 30 is provided with a thumb ring 34 and a longitudinal bore 36 is provided at the distal end of the shaft 30. A longitudinal slot 38 extends from the proximal end of bore 36 to a point distal of the thumb ring 34. The displaceable spool 32 is provided with a cross member 40 which passes through the slot 38 in the central shaft 30. The cross member 40 is provided with a central through hole 42 and a radially engaging set screw 44. A first electrical contact 46 is provided on the spool 32 and extends radially outward from the set screw 44 through a protective insulating collar 48. The longitudinal bore 36 is provided with a second electrical contact 50 which extends radially outward from the interior of the bore 36. As shown in FIG. 1, the proximal end 14 of the conductive hollow tube 12 is mounted in the longitudinal bore 36 and makes electrical contact with the electrical connector 50. The proximal end 20 of the conductive pull wire 18 is mounted in the hole 42 of the cross member 40 by the set screw 44 and makes electrical contact with the electrical connector 46.

Figure 3:
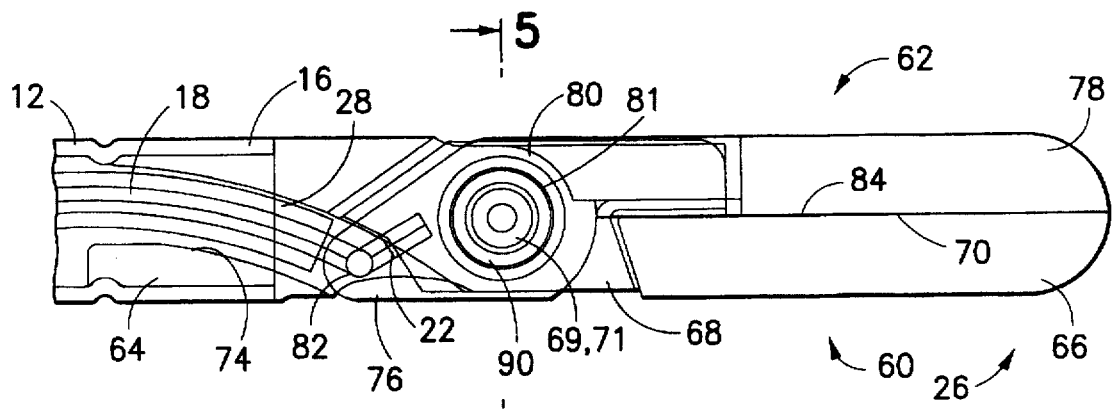
FIG. 3 is an enlarged broken transparent view of the end effectors of FIG. 1 looking parallel to the axis of rotation with the forceps in the closed position.

Turning now to FIGS. 2–5, the end effector assembly 26 includes a first stationary end effector 60 and a second rotatable end effector 62, both of which are preferably made of cast alloy. The first end effector 60 has a proximal shank portion 64, a distal gripper portion 66, and an intermediate mounting portion 68 having an integral axle pin 69 with a spreadable rivet-like end 71. The proximal shank portion 64 is substantially cylindrical and is press fit or crimped into the distal end 16 of the hollow conductive tube 12 (FIGS. 1, 3). The distal gripper portion 66 has a substantially planar gripping surface 70 lying in a first plane, and the intermediate mounting portion 68 has a substantially planar surface 72 lying in a second plane which is substantially orthogonal to the first plane. According to one aspect of the invention, and as seen best in FIG. 3, the proximal shank portion 64 is provided with a curved guiding channel 74 through which the conductive pull wire 18 is guided as described more fully below. According to another aspect of the invention, and as seen best in FIG. 5, substantially all of the first end effector 60, except for its gripping surface 70 and its proximal shank portion 64, is coated with electrically insulating polymer 61, such as PTFE.

Figure 5:
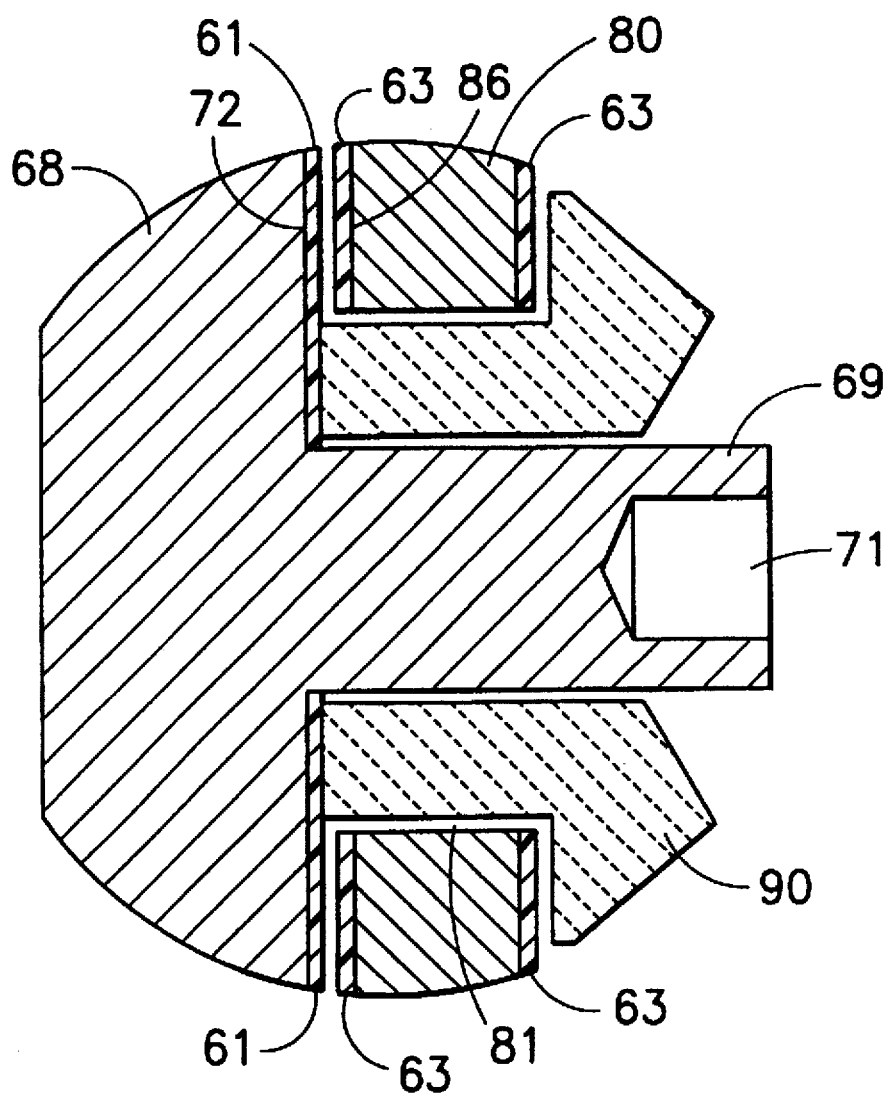
FIG. 5 is an enlarged cross sectional view taken along line 5—5 in FIG. 3.
Figure 5A:
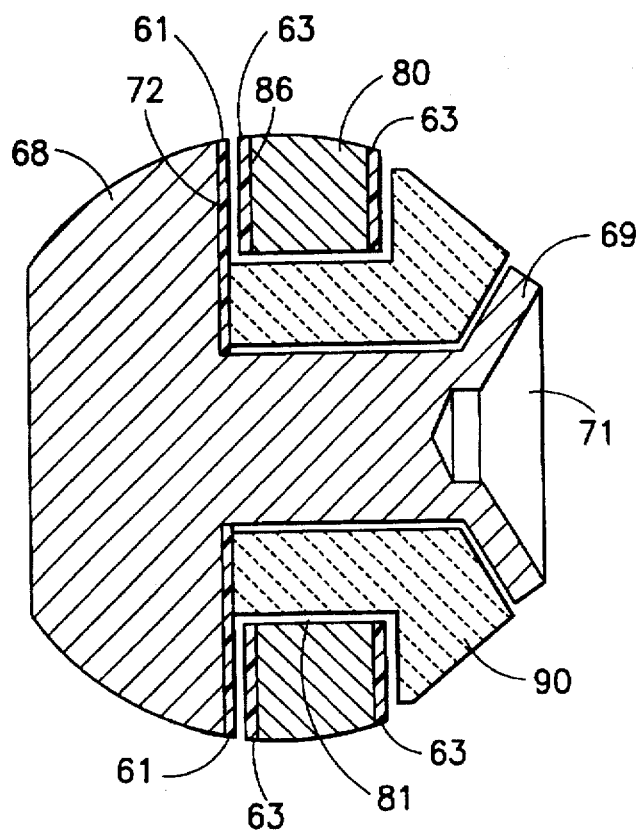
FIG. 5a is a view similar to FIG. 5 with the end of the rivet spread.

The second end effector 62 has a proximal tang 76, a distal gripper portion 78, and an intermediate mounting portion 80 with a mounting hole 81 for rotatably mounting it on the mounting portion 68 of the first end effector 60. The proximal tang 76 is provided with a pull wire hole 82 for coupling to the distal end 22 of the pull wire 18, and the distal gripper portion 78 has a substantially planar gripping surface 84 lying in a first plane. The intermediate mounting portion 80 has a substantially planar surface 86 lying in a second plane which is substantially orthogonal to the first plane. According to the invention, and as seen best in FIG. 5, substantially all of the second end effector 62, except for its gripping surface 84 and its proximal tang 76, is coated with electrically insulating polymer 63 such as PTFE. Also, as seen best in FIG. 5, the second end effector 62 is rotatably mounted on the axle pin 69 of the first end effector 60 by placing a ceramic bushing-washer 90 between the axle pin 69 and the mounting hole 81 before spreading the end 71 of the pin 69 (as seen in FIG. 5a). The distal end 22 of the pull wire 18 is coupled to the hole 82 in the tang 80 of the second end effector 62 by creating a Z-bend in the wire as seen best in FIG. 2.

Figure 5B:
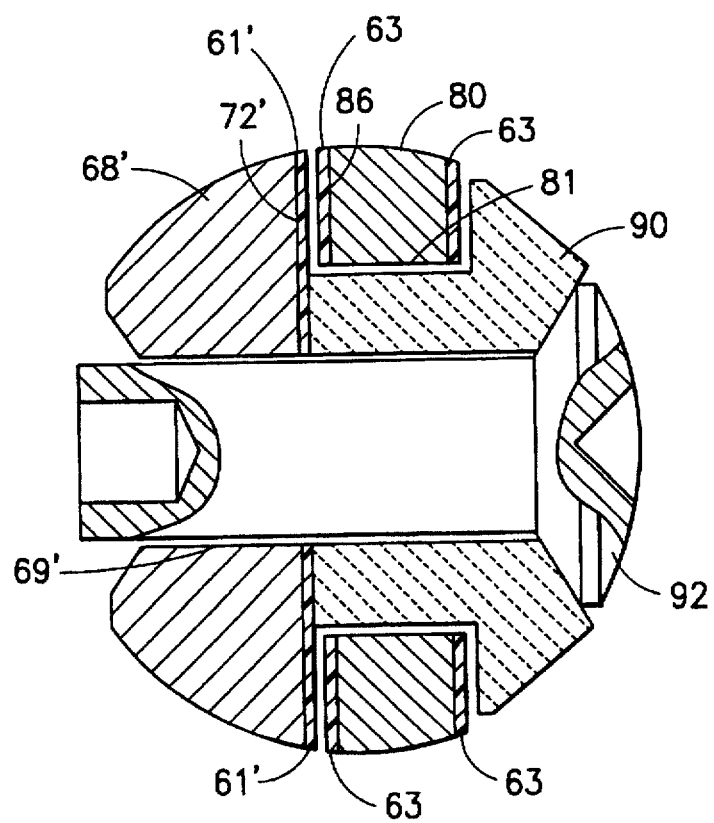
FIG. 5b is a view similar to FIG. 5 of an alternate embodiment of the invention.

An alternative embodiment for mounting the second end effector on the first end effector is shown in FIG. 5b. In this embodiment, the mounting portion 68' of the first end effector is provided with a mounting hole 69'. A stainless steel rivet 92 is inserted through the ceramic bushing-washer 90 which is inserted through the hole 81 in the mounting portion 80 of the second end effector. The end of the rivet 92 is inserted through the hole 69' in the mounting portion 68' of the first end effector and its end is spread.

From the foregoing, it will be appreciated that the first end effector 60 makes an electrical connection through its shank 64 with the distal end 16 of the tube 12, and the second end effector 62 makes an electrical connection with the distal end 22 of the pull wire 18. It will also be appreciated that the pull wire 18 is insulated from the tube 12 and from the shank 64 of the first end effector 60 by its insulative covering 18. The end effectors are substantially insulated from each other by their respective PTFE coatings and by the ceramic bushing-washer 90 when the end effectors are in the open position shown in FIG. 4.

Figure 4:
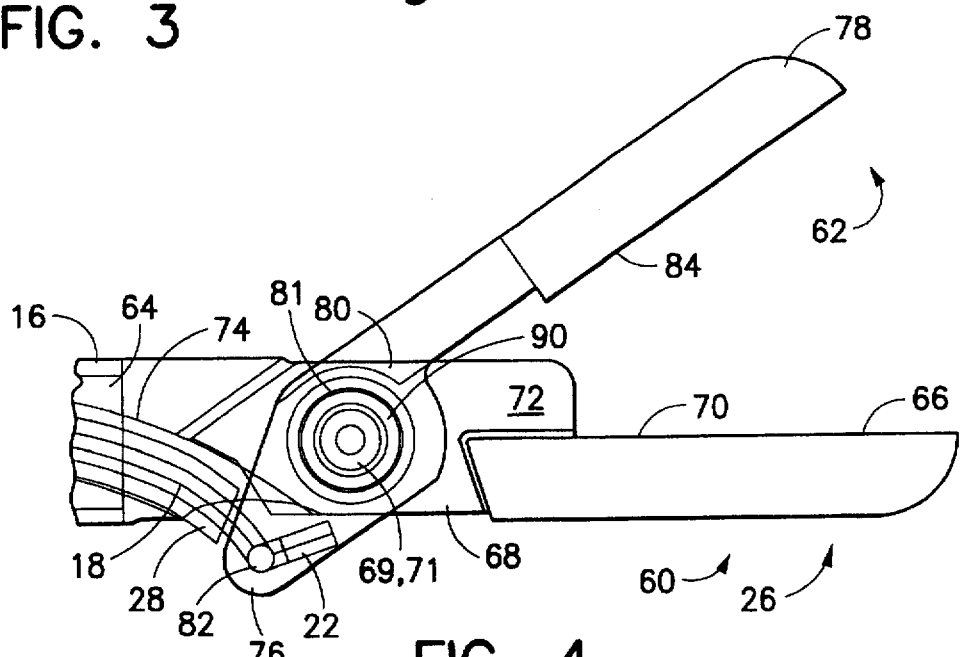
FIG. 4 is a view similar to FIG. 3 with the forceps in the open position.

It will further be appreciated that translational movement of the pull wire 18 through the tube 12 by means of the actuator 24 (FIG. 1), will result in a rotational movement of the second end effector 62 relative to the first end effector 60 to open and close the end effectors as seen in FIGS. 3 and 4. As seen best in FIGS. 3 and 4, the pull wire 18 must move out of the tube in a radial as well as an axial direction. The guiding channel 74 supports and directs the movement of the relatively flexible pull wire 18 to maximize the rotational moment of the jaw 78 within the small dimensional parameters of the instrument. In supporting and directing the pull wire, the guiding channel 74 prevents the thin pull wire 18 from kinking. In addition, in the preferred embodiment of the invention, where the pull wire 18 is insulated by insulation 18, the provision of the guiding channel minimizes the possibility that the insulative covering 18 will frictionally engage an edge of the tube and become worn away resulting in a short circuit. Thus, the curved guiding channel 74 in the shank 64 of the first end effector 60 provides a smooth path for insulated pull wire 18.

In use, the end effectors will be placed in the open position shown in FIG. 4 and guided to a tissue (not shown). The end effectors will then be closed upon the tissue so that the non-insulated gripping surfaces 70, 84 of the end effectors grasp the tissue. Bipolar cautery current will then be applied to the tissue through the end effectors via the electrical couplings 46, 50 shown in FIG. 1.

There have been described and illustrated herein several embodiments of a bipolar endoscopic forceps which has particular usefulness in neurological procedures. While particular embodiments of the invention have been described, it is not intended that the invention be limited thereto, as it is intended that the invention be as broad in scope as the art will allow and that the specification be read likewise. Thus, while a particular spool and thumb ring type of actuator has been disclosed, it will be appreciated that other actuators such as, e.g., a conventional scissor grip actuator, could be utilized. Also, while the end effectors have been described as forceps having substantially planar gripping surfaces, it will be recognized that other configurations of gripping surfaces could be used, and that other types of end effectors (e.g., scissors) could be utilized. In addition, while a stationary end effector fitting into the tube and having an arcuate guiding path has been shown and described, it will be appreciated that the tube can fit over the proximal end of the stationary end effector, and the tube can be provided at its distal end with the guiding path rather than the proximal end of the end effector being provided with the guiding path. Moreover, while particular configurations have been disclosed in reference to electrical couplings in the actuator, it will be appreciated that other configurations could be used as well. Furthermore, while the end effectors have been disclosed as being substantially completely coated with PTFE except for their electrical connections and their gripping surfaces, it will be understood that coating the end effectors only on their respective contact surfaces can achieve the same or similar function as disclosed herein. In fact, if cautery capability is not required, the electrical couplings, and end effector coatings are not required. It will therefore be appreciated by those skilled in the art that yet other modifications could be made to the provided invention without deviating from its spirit and scope as so claimed.

We claim:

1. A small diameter endoscopic instrument, comprising:
 a) a hollow tube having a proximal end and a distal end;
 b) an axially displaceable flexible wire extending through said hollow tube, said wire having a proximal end and a distal end;
 c) a manual actuation means coupled to the proximal ends of said tube and said wire for axially displacing one of said tube and said wire relative to the other;
 d) a first end effector mechanically coupled to said distal end of said tube; and
 e) a second end effector mechanically coupled to said distal end of said wire and rotatably coupled to said first end effector, wherein a curved guiding channel is provided in either a proximal portion of said first end effector or a distal portion of said hollow tube, and said axially displaceable wire extending through said channel and is guided by said channel to move radially as well as axially when said manual actuation means axially displaces one of said tube and said wire relative to the other, said guiding channel being in a fixed orientation relative to said distal end of said hollow tube.

2. An endoscopic instrument according to claim 1, wherein:
 said hollow tube has an outer diameter of at most approximately 2.0 mm.

3. An endoscopic instrument according to claim 1, wherein:
 said tube and said wire are conductive,
 said wire is covered with an electrically insulating sheath,
 said first end effector is conductive and partially insulated, and electrically coupled to said tube, and
 said second end effector is conductive and partially insulated, and electrically coupled to said wire.

4. An endoscopic instrument according to claim 3, wherein:
 said first end effector and said second end effector are forceps.

5. An endoscopic instrument according to claim 3, wherein:
 said manual actuation means is provided with a pair of electrical couplings for coupling respective poles of a source of bipolar cautery to said tube and wire.

6. An endoscopic instrument according to claim 5, wherein:
 said manual actuation means comprises a slotted shaft and a displaceable spool.

7. An endoscopic instrument according to claim 6, wherein:
 said pair of electrical couplings comprises an electrical coupling on said displaceable spool electrically coupled to said axially displaceable conductive wire and an electrical coupling on said slotted shaft electrically coupled to said hollow conductive tube.

8. An endoscopic instrument according to claim 3, wherein:
 said first and second end effectors are cast alloy and are partially coated with PTFE.

9. An endoscopic instrument according to claim 3, wherein:
 said second end effector is rotatably coupled to said first end effector by means of an axle pin and an insulating ceramic bushing which electrically insulates said axle pin from one of said first and second end effectors.

10. An endoscopic instrument according to claim 9, wherein:
 said axle pin is an integral part of one of said first and second end effectors.

11. An endoscopic instrument according to claim 3, wherein:
 said curved guiding channel is formed in said proximal portion of said first end effector.

12. A bipolar endoscopic instrument, comprising:
 a) a hollow conductive tube having a proximal end and a distal end;
 b) an axially displaceable conductive wire extending through said hollow tube and covered with an electrically insulating sheath, said axially displaceable wire having a proximal end and a distal end;

c) a manual actuation means coupled to the proximal ends of said tube and said wire for axially displacing one of said tube and said wire relative to the other;

d) a first conductive partially insulated end effector mechanically and electrically coupled to said distal end of said tube;

e) a second conductive partially insulated end effector mechanically and electrically coupled to said distal end of said wire and rotatably coupled to said first end effector; and f) an insulating ceramic bushing, wherein said second end effector is rotatably coupled to said first end effector by means of an axle pin which is integral with one of said first and second end effectors, said insulating ceramic bushing extending over said axle pin and electrically insulating said axle pin from the other of said first and second end effectors.

13. An endoscopic instrument according to claim 12, wherein:

said hollow tube has an outer diameter of at most approximately 2.0 mm.

14. An endoscopic instrument according to claim 12, wherein:

said manual actuation means is provided with a pair of electrical couplings for coupling respective poles of a source of bipolar cautery to said tube and wire.

15. An endoscopic instrument according to claim 14, wherein:

said manual actuation means comprises a slotted shaft and a displaceable spool.

16. An endoscopic instrument according to claim 15, wherein:

said pair of electrical couplings comprises an electrical coupling on said displaceable spool electrically coupled to said axially displaceable conductive wire and an electrical coupling on said slotted shaft electrically coupled to said hollow conductive tube.

17. An endoscopic instrument according to claim 12, wherein:

said first and second end effectors are cast alloy and are partially coated with PTFE.

18. An endoscopic instrument according to claim 17, wherein:

said first and second end effectors are forceps.

19. An endoscopic instrument according to claim 12, wherein:

a curved guiding channel is provided in either a proximal portion of said first end effector or a distal portion of said hollow conductive tube, and said axially displaceable conductive wire extends through said channel and is guided by said channel to move radially as well as axially when said manual actuation means axially displaces one of said tube and said wire relative to the other.

20. An endoscopic instrument according to claim 12, wherein:

said first and second effectors are forceps.

* * * * *